United States Patent [19]

Gentilcore

[11] Patent Number: 4,724,103

[45] Date of Patent: Feb. 9, 1988

[54] PROCESS FOR PREPARING N,N-DIACETIC ACID AMINOMETHYLENEPHOSPHONIC ACID

[75] Inventor: Michael J. Gentilcore, St. Louis, Mo.

[73] Assignee: Monsanto Company, St. Louis, Mo.

[21] Appl. No.: 676,749

[22] Filed: Dec. 5, 1984

Related U.S. Application Data

[63] Continuation-in-part of Ser. No. 584,038, Feb. 27, 1984, abandoned.

[51] Int. Cl.$^4$ .................................................. C07F 9/38
[52] U.S. Cl. .................................................. 260/502.5 F
[58] Field of Search ..................................... 260/502.5 F

[56] References Cited

U.S. PATENT DOCUMENTS

| | | | |
|---|---|---|---|
| 2,609,390 | 9/1952 | Bersworth | 260/502.5 F |
| 3,288,846 | 11/1966 | Irani et al. | 260/502.5 F |
| 3,904,668 | 9/1975 | Gaudette et al. | 260/465.5 A |
| 4,237,065 | 12/1980 | Ehrat | 260/502.5 F |
| 4,389,349 | 6/1983 | Cho et al. | 260/502.5 F |

FOREIGN PATENT DOCUMENTS

| | | | |
|---|---|---|---|
| 766459 | 9/1971 | Belgium | 260/502.5 F |
| 1142294 | 2/1969 | United Kingdom | 260/502.5 F |
| 1575469 | 9/1980 | United Kingdom | |

*Primary Examiner*—J. E. Evans
*Attorney, Agent, or Firm*—Frank D. Shearin; Raymond C. Loyer

[57] ABSTRACT

An energy saving process for preparing N,N-diacetic acid aminomethylenephosphonic acid by reacting an alkali metal salt of iminodiacetic acid in aqueous strong mineral acid solution with phosphorous acid and formaldehyde and then adding sufficient water to dissolve the alkali metal salt formed during the reaction. The desired product is recovered as a precipitate from the solution.

8 Claims, No Drawings

PROCESS FOR PREPARING N,N-DIACETIC ACID AMINOMETHYLENEPHOSPHONIC ACID

This is a continuation-in-part of application Ser. No. 584,038, filed Feb. 27, 1984, now abandoned.

BACKGROUND OF THE INVENTION

The present invention relates to an improved process for preparing N,N-diacetic acid aminomethylenephosphonic acid also known chemically as N-phosphonomethyliminodiacetic acid of the formula (I):

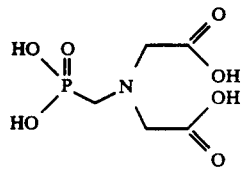

The above compound (I) is an intermediate in the preparation of N-phosphonomethylglycine (glyphosate), an important broad spectrum herbicide. More particularly, the present invention relates to an improved chemical route to (I) in which iminodiacetonitrile (IDAN) is the starting material. IDAN has previously been converted to iminodiacetic acid (IDA) by various process steps beginning with hydrolysis of IDAN with an alkali metal hydroxide, usually sodium hydroxide. This process is described in U.S. Pat. No. 3,904,668.

The practice heretofore in the preparation of IDA for utilization in a phosphonomethylation process to produce N,N-diacetic acid aminomethylenephosphonic acid was to recover IDA from the crude hydrolysate of IDAN by (1) acidification with a mineral acid (typically sulfuric or hydrochloric acid), (2) crystallization of IDA, (3) filtration to recover the crystallized IDA, and (4) drying the IDA for packaging, shipping, etc. A similar recovery of IDA is taught in British Patent No. 1,575,469. Also, the sodium salt solution separated from IDA in (3) above contained unrecovered IDA which was recovered by evaporating water from the solution resulting in precipitation of sodium salt while leaving the IDA in solution. The precipitated sodium salt was then separated from the residue by filtration and the filtrate recycled to Step (1) above. The above-described process is energy intensive and requires a large investment for the acquisition and maintenance of equipment to recover and purify IDA.

In the past, the recovered IDA from (4) above was utilized in a phosphonomethylation process such as that disclosed in U.S. Pat. No. 3,288,846 to Irani et al, particularly Example IV. In such process the hydrochloride salt is initially formed which is then phosphonomethylated with phosphorous acid ($H_3PO_3$) and formaldehyde ($CH_2O$). In an alternate method the hydrogen chloride employed to form the hydrochloride salt of IDA and the phosphorous acid employed in phosphonomethylation are provided by the addition of phosphorus trichloride to water. In water, phosphorus trichloride is hydrolyzed to form hydrogen chloride and phosphorous acid. After phosphonomethylation the desired N,N-diacetic acid aminomethylenephosphonic acid is recovered from the reaction mixture by crystallization and filtration. Under current practice there is sufficient unreacted material in the filtrate to require recycle of the filtrate. A large amount of hydrogen chloride is released during the hydrolysis of phosphorus trichloride, if employed, and is recovered.

Although the above-described procedures are commercially feasible, the need for a reduction in the amount of energy consumed and equipment required makes further improvement highly desirable.

SUMMARY OF THE INVENTION

In accordance with the present invention there is provided an improved process for preparing N,N-diacetic acid aminomethylenephosphonic acid (1) wherein IDAN is hydrolyzed with an alkali metal base to form an alkali metal salt of IDA which is converted to IDA strong acid salt and phosphonomethylated. The improvement comprises reacting in series the alkali metal salt of IDA with a strong mineral acid to form the strong acid salt of IDA and the alkali metal salt of the strong acid and then phosphonomethylating by reacting the strong acid salt of IDA with phosphorous acid and formaldehyde to provide (1) and an alkali metal salt. Then an amount of water is added to the reaction mixture sufficient to dissolve the alkali metal salt and (I) is separated as a precipitate.

Further within the scope of this invention, it has been discovered that the hydrolysate of IDAN containing the alkali metal salt of IDA can be employed directly in the above-described improved process resulting in the production of (I) in high yield and purity. Surprisingly, it has been found that there is no need to isolate the alkali metal salt of IDA from the crude hydrolysate.

Because of the elimination of numerous steps for the conversion, purification, and recovery of IDA from the crude hydrolysate of IDAN, the process of this invention offers a more economical route to (1) than previously known.

DETAILED DESCRIPTION OF THE INVENTION

According to the process of this invention, N,N-diacetic acid aminomethylenephosphonic acid can be prepared from the alkali salt of iminodiacetic acid, preferably $Na_2IDA$, by first converting the alkali metal salt to the strong acid salt of IDA and the alkali metal salt of the strong acid.

As employed herein the term "strong mineral acid" includes those mineral acids having a pKa lower than phosphorous acid employed in the phosphonomethylation step. Typical such acids include sulfuric acid, hydrochloric acid, hydrobromic acid, hydroiodic acid and the like. Hydrochloric acid is preferred because it is most economical when provided by conversion of phosphorus trichloride in situ as further explained below. Sulfuric acid is preferred when phosphorous acid is employed directly. Because hydrochloric acid is preferred, the invention will be further described with reference to hydrochloric acid although any other suitable strong mineral acid can be employed in its place.

Although the process of this invention is described with $Na_2IDA$ as a starting material, other IDA alkali salts, such as $K_2IDA$, may also be used.

In a preferred embodiment phosphorus trichloride is hydrolyzed to phosphorous acid while the $Na_2IDA$ is simultaneously transformed to iminodiacetic acid hydrochloride (IDA.HCl) and sodium chloride according to the following general equations:

$$PCl_3 + 3H_2O \rightarrow H_3PO_3 + 3HCl$$

$$Na_2IDA + 2HCl \rightarrow IDA + 2NaCl$$

$$IDA + HCl \rightleftharpoons IDA.HCl$$

The reaction is best carried out at reflux temperatures of about 110°–120° C. Lower temperatures can be used, but this tends to reduce the evolution of HCl and the reaction mixture would tend to thicken and make agitation difficult. Alternatively HCl and phosphorous acid can be combined with Na₂IDA to form IDA.HCl and sodium chloride.

In this reaction the phosphorus trichloride is hydrolyzed to phosphorous acid in the Na₂IDA solution and a slurry is formed. HCl, which results from hydrolysis of phosphorus trichloride, acidifies the Na₂IDA to its hydrochloride salt and to NaCl, both of which precipitate. Optionally, additional HCl can be added to ensure complete formation of the IDA hydrochloride salt. The amount of additional HCl which can be added can be determined by procedures well known in the art.

The concentration of the Na₂IDA solution is an important variable in the process. Preferably, concentration should be in the range of 38–44% Na₂IDA by weight. Higher concentrations can be used, but these may be undesirable because the slurry formed in the PCl₃ hydrolysis step will tend to thicken and be hard to agitate. Lower concentrations (<38% Na₂IDA) can be used, but this tends to reduce yield because more IDA will be left unreacted in the phosphonomethylation step.

The IDA ®HCl in the reaction mixture is then phosphonomethylated by adding formaldehyde (CH₂O) thereto. For convenience, formalin, a 44% by weight CH₂O solution stabilized with 1% MeOH, can be used in this step, although all sources of formaldehyde would be satisfactory for practicing this invention, e.g., paraformaldehyde. The reaction proceeds according to the following equation:

$$H_3PO_3l + CH_2O + IDA.HCl \rightarrow$$
$$(HO_2)P(O)CH_2N(CH_2COOH)_2 + H_2O + HCl.$$

Ordinarily, phosphonomethylation is conducted at reflux temperatures ranging from 108°–120° C.

To ensure high conversion of IDA during phosphonomethylation, formaldehyde and phosphorous acid should be in stoichiometric excess. Generally, the mole ratio of phosphorus trichloride to alkali metal iminodiacetic acid is in the range of from about 0.8 to about 1.4. A 1.1 mole ratio of PCl₃ to IDA and a 1.2 mole ratio of formaldehyde to IDA are preferred.

Under certain conditions IDA and CH₂O can react to form N-methyl iminodiacetic acid (N-Me IDA) an undesired by-product.

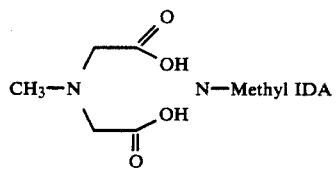

N—Methyl IDA

This type of side reaction can be minimized with sufficient strong mineral acid, preferably HCl, in the reaction mixture. In the preferred process with HCl as the only strong mineral acid present, the concentration of HCl in excess of the hydrochloride salt of IDA in the reaction mass should be at least 5% by weight (calculated on the basis of HCl and H₂O, only), although it may range from 0% to 20%.

In the preferred embodiment of this invention it is preferable to add a portion of the total Na₂IDA charge along with the CH₂O during the phosphonomethylation step. The Na₂IDA will be acidified by the liberated HCl according to the reaction shown below.

$$IDA.HCl + CH_2O + H_3PO_3 \rightarrow (I) + HCl + H_2O$$

By adding Na₂IDA during the phosphonomethylation step it is possible to minimize the amount of acid necessary in the phosphonomethylation step without substantially increasing by-product N-Me IDA. The Na₂IDA can be added without noticeable increased formation of N-Me IDA as long as the concentration of HCl in excess of the hydrochloride salt of IDA is at or above at least 5% (calculated on the basis of HCl and H₂O, only). Addition of Na₂IDA during the phosphonomethylation step has the further advantage of utilizing hydrogen chloride more efficiently. During phosphonomethylation hydrogen chloride is given off and is utilized to convert the additional Na₂IDA to the hydrochloride salt of IDA. Preferably, 20% to 25% of the total charge of Na₂IDA can be added during the phosphonomethylation step.

A by-product of this process is sodium salt of a strong mineral acid. In a preferred embodiment following phosphonomethylation, a dilute base, such as sodium hydroxide, is added to the reaction mixture so that the pH of the mixture is adjusted to the isoelectric point of the N,N-diacetic acid aminomethylenephosphonic acid, i.e., the point of minimum solubility. The charge of base is most conveniently determined by calculation. The amount of base is such that approximately all the HCl in the reaction mixture is neutralized. The concentration of the base is such that sufficient water is present to dissolve all by-product NaCl in the final mixture. The calculations are well known to those skilled in the art.

In the reaction product, N,N-diacetic acid aminomethylenephosphonic acid is present as a solid precipitate. It can be separated from the mixture by filtration and then washed and dried. The N,N-diacetic acid aminomethylenephosphonic acid is obtained in high yield at a cost and energy usage significantly below that of known commercial processes which begin with IDAN as a starting material and wherein IDA is isolated from the crude hydrolysate.

The process of this invention is illustrated in the following examples in which concentrations are by weight and temperature is in ° C. unless otherwise indicated. A 500 ml round bottom flask complete with condenser, agitator, heating mantle and temperature regulating means was used as the reactor in all examples. Fhosphorus trichloride and formaldehyde were charged via 50 cc syringes and a syringe pump. Filtering was done on an 11 cm diameter porcelain filter with Whatman #3 qualitative filter paper. Pressure was atmospheric.

In the following representative examples the Na₂IDA solution employed was a crude hydrolysate of IDAN. The crude hydrolysate was obtained by hydrolyzing IDAN in sodium hydroxide solution using a mole ratio of sodium hydroxide to IDAN of about 2.5. The hydrolysis was performed under vacuum to strip out the by-product NH₃. In Example 2, the Na₂IDA solution composition was adjusted slightly, prior to use, by atmospheric evaporation and addition of a small amount of IDA to increase Na$_2$IDA content and reduce NaOH content.

EXAMPLE 1

184.0 g of Na$_2$IDA solution was charged to the reactor. The solution analyzed 37.96% Na$_2$IDA and 4.37% NaOH by simple titration. IDA assay by HPLC analysis was 28.25%. 17.4 g of 37% HCl was then added. The mixture was heated to boiling, and 11 ml of water was distilled.

With the temperature controlled at 110°–112° C., 64 g of PCl$_3$ was added at a rate of 0.764 ml/min. The composition at the end of the PCl$_3$ addition was calculated to be: 66.9 9 IDA HCl, 57.93 9 NaCl, 6.86 g HCl, 84.55 g H$_2$O, and 38.17 g H$_3$PO$_3$. The concentration of HCl was 7.5% (HCl and H$_2$O basis).

With the temperature controlled at 108°–110° C., 32.0 g or 44% CH$_2$O (as formalin) was added over a period of 1 hour. The mixture was held an additional 90 minutes after the formalin addition was complete.

The mixture was cooled with an ice bath during which 190.80 g of 12.2% NaOH aqueous solution was added. The temperature of the cooled mixture was 15° C.

The mixture was filtered, and a wet cake was recovered which was washed with 46 g H$_2$O and dried. 78.21 g of dry solids were recovered. Product assayed 99.75% N,N-diacetic acid aminomethylenephosphonic acid. Isolated yield was 87.9% [(78.21 × 0.9975)/(184.0×0.2825)×133/227].

EXAMPLE 2

159.96 g of Na$_2$IDA solution were charged to the reactor. The solution was analyzed as in Example 1 and found to contain 41.85% Na$_2$IDA and 1.95% NaOH.

The solution was heated to reflux (113° C). 73.13 g of PCl$_3$ were added at 745 ml/min. The mixture was maintained at refluxing conditions throughout the PCl$_3$ addition. Near the end of the PCl$_3$ addition, 3.5 g of HCl was evolved and collected in a water scrubber. The temperature at the end of the PCl$_3$ addition was 117° C.

With the temperature controlled at 108°–110° C., 38.8 g of 44% formalin and 40.23 g of Na$_2$IDA solution were added to the batch. The formalin was added uniformly over a period of 68 minutes. The Na$_2$IDA solution was added uniformly over 60 minutes. The addition of Na$_2$IDA solution was started 3 minutes after the start of formalin addition. The batch was then held an additional 90 minutes after the end of the formalin addition.

The batch was allowed to cool to 45° C. During the cool down, 145.75 g of 10.7% NaOH were added. The batch was filtered. The recovered wet cake was washed with 105 ml of water and dried. 97.88 g of 98.4% assay N,N-diacetic acid aminomethylenephosphonic acid was recovered. Isolated yield was 89.6% (97.88×0.984)/((159.96+40.23)×4185)×177/227.

Although the present invention has been described above with respect to several embodiments, the details are not to be construed as limitations except as to the extent indicated in the following claims.

What is claimed is

1. A process for preparing N,N-diacetic acid aminomethylenephosphonic acid which comprises reacting in series, an alkali metal salt of iminodiacetic acid with a strong mineral acid to form the strong mineral acid salt of iminodiacetic acid and the alkali metal salt of the strong mineral acid and phosphonomethylating the salt of iminodiacetic acid by reaction with formaldehyde and phosphorous acid to provide a mixture of N,N-diacetic acid aminomethylenephosphonic acid and an alkali metal salt; after the phosphonomethylation step adding an amount of water to the reaction mixture sufficient to dissolve the alkali metal salt and separating said N,N-diacetic acid aminomethylenephosphonic acid as a precipitate.

2. The process of claim 1 wherein the strong mineral acid is hydrochloric acid.

3. The process of claim 2 wherein the alkali metal salt of iminodiacetic acid is the disodium salt.

4. The process of claim 1 wherein the alkali metal salt of iminodiacetic acid is the dipotassium salt.

5. The process of claim 3 wherein the hydrogen chloride and phosphorous acid is provided by adding phosphorus trichloride to an aqueous reaction medium.

6. The process of claim 5 wherein the phosphorus trichloride and the total amount of disodium salt of iminodiacetic acid are present in the reaction mixture in the mole ratio of about 0.8 to 1.4.

7. The process of claim 1 wherein the water added after the phosphonomethylation step contains an amount of base so as to neutralize excess strong mineral acid in the reaction mixture.

8. A process of claim 1 wherein the alkali metal salt of iminodiacetic acid is the disodium salt.

* * * * *